(12) United States Patent
Penner (10) Patent No.: US 8,078,278 B2
(45) Date of Patent: Dec. 13, 2011

(54) BODY ATTACHABLE UNIT IN WIRELESS COMMUNICATION WITH IMPLANTABLE DEVICES

(75) Inventor: Abraham Penner, Tel Aviv (IL)

(73) Assignee: Remon Medical Technologies Ltd., Caesarea (IL)

( * ) Notice: Subject to any disclaimer, the term of this patent is extended or adjusted under 35 U.S.C. 154(b) by 546 days.

(21) Appl. No.: 11/373,005

(22) Filed: Mar. 10, 2006

(65) Prior Publication Data
US 2007/0162090 A1 Jul. 12, 2007

Related U.S. Application Data (60) Provisional application No. 60/757,712, filed on Jan. 10, 2006.

(51) Int. Cl.
*A61N 1/37* (2006.01)
(52) U.S. Cl. ......................................................... 607/32
(58) Field of Classification Search .............. 607/30–32, 607/60
See application file for complete search history.

(56) References Cited

U.S. PATENT DOCUMENTS

| | | | |
|---|---|---|---|
| 2,786,899 A | 3/1957 | Carlisle et al. |
| 3,536,836 A | 10/1970 | Pfeiffer |
| 3,672,352 A | 6/1972 | Summers |
| 3,757,770 A | 9/1973 | Brayshaw et al. |
| 3,805,796 A | 4/1974 | Terry, Jr. et al. |
| 3,853,117 A | 12/1974 | Murr |
| 3,943,915 A | 3/1976 | Severson |
| 3,970,987 A | 7/1976 | Kolm |
| 4,026,276 A | 5/1977 | Chubbuck |
| 4,041,954 A | 8/1977 | Ohara |
| 4,062,354 A | 12/1977 | Taylor et al. |
| 4,082,097 A | 4/1978 | Mann et al. |
| 4,099,530 A | 7/1978 | Chen et al. |
| 4,127,110 A | 11/1978 | Bullara |
| 4,170,742 A | 10/1979 | Itagaki et al. |
| 4,206,761 A | 6/1980 | Cosman |
| 4,206,762 A | 6/1980 | Cosman |
| 4,265,252 A | 5/1981 | Chubbuck et al. |

(Continued)

FOREIGN PATENT DOCUMENTS

EP 0 499 939 8/1992

(Continued)

OTHER PUBLICATIONS

PCT International Search Report for PCT/IB2007/000052, Applicant: Remon Medical Technologies Ltd., Form PCT/ISA/210 and 220, dated Jun. 21, 2007 (6 pages).

(Continued)

*Primary Examiner* — Scott Getzow
*Assistant Examiner* — Amanda Patton
(74) *Attorney, Agent, or Firm* — Faegre & Benson LLP (57) ABSTRACT

Medical systems and devices are provided. A medical system includes implantable devices and an external device configured for wirelessly interacting with the implantable devices. The external device may be attachable to a patient and be configured for wirelessly communicating with a first implantable device, e.g., using acoustic energy, and wirelessly interacting with a second implantable device, e.g., using non-acoustic energy. The first implantable device may be a diagnostic device, in which case, the external device may wirelessly receive physiological information from the diagnostic device, and the second implantable device may be a therapeutic device, in which case, the external device may wirelessly interact with the therapeutic device to provide or optimize therapy to a patient.

20 Claims, 7 Drawing Sheets

U.S. PATENT DOCUMENTS

| | | |
|---|---|---|
| 4,281,666 A | 8/1981 | Cosman |
| 4,281,667 A | 8/1981 | Cosman |
| 4,340,038 A | 7/1982 | Mc Kean |
| 4,354,506 A | 10/1982 | Sakaguchi et al. |
| 4,361,153 A | 11/1982 | Slocum et al. |
| 4,378,809 A | 4/1983 | Cosman |
| 4,385,636 A | 5/1983 | Cosman |
| 4,407,296 A | 10/1983 | Anderson |
| 4,471,786 A | 9/1984 | Inagaki et al. |
| 4,481,950 A | 11/1984 | Duggan |
| 4,494,950 A | 1/1985 | Fischell |
| 4,519,401 A | 5/1985 | Ko et al. |
| 4,556,061 A | 12/1985 | Barreras et al. |
| 4,593,703 A | 6/1986 | Cosman |
| 4,596,255 A * | 6/1986 | Snell et al. ............... 600/510 |
| 4,614,192 A | 9/1986 | Imran et al. |
| 4,616,640 A | 10/1986 | Kaali et al. |
| 4,651,740 A | 3/1987 | Schroeppel |
| 4,653,508 A | 3/1987 | Cosman |
| 4,660,568 A | 4/1987 | Cosman |
| 4,676,255 A | 6/1987 | Cosman |
| 4,677,985 A | 7/1987 | Bro et al. |
| 4,708,127 A | 11/1987 | Abdelghani |
| 4,719,919 A | 1/1988 | Marchosky et al. |
| 4,791,915 A | 12/1988 | Barsotti et al. |
| 4,791,936 A | 12/1988 | Snell et al. |
| 4,793,825 A | 12/1988 | Benjamin et al. |
| 4,869,251 A | 9/1989 | Lekholm et al. |
| 4,885,002 A | 12/1989 | Watanabe et al. |
| 4,911,217 A | 3/1990 | Dunn et al. |
| 4,918,736 A | 4/1990 | Bordewijk |
| 5,074,310 A | 12/1991 | Mick |
| 5,113,859 A | 5/1992 | Funke |
| 5,117,835 A | 6/1992 | Mick |
| 5,160,870 A | 11/1992 | Carson et al. |
| 5,168,869 A | 12/1992 | Chirife |
| 5,184,605 A | 2/1993 | Grzeszykowski |
| 5,218,861 A | 6/1993 | Brown et al. |
| 5,279,292 A | 1/1994 | Baumann et al. |
| 5,291,899 A | 3/1994 | Watanabe et al. |
| 5,381,067 A | 1/1995 | Greenstein et al. |
| 5,423,334 A | 6/1995 | Jordan |
| 5,433,736 A | 7/1995 | Nilsson |
| 5,445,150 A | 8/1995 | Dumoulin et al. |
| 5,495,453 A | 2/1996 | Wojciechowski et al. |
| 5,562,621 A | 10/1996 | Claude et al. |
| 5,619,997 A | 4/1997 | Kaplan |
| 5,620,475 A | 4/1997 | Magnusson |
| 5,704,352 A | 1/1998 | Tremblay et al. |
| 5,704,366 A | 1/1998 | Tacklind et al. |
| 5,712,917 A | 1/1998 | Offutt |
| 5,721,886 A | 2/1998 | Miller |
| 5,724,985 A * | 3/1998 | Snell et al. ............... 600/510 |
| 5,743,267 A | 4/1998 | Nikolic et al. |
| 5,749,909 A | 5/1998 | Schroeppel et al. |
| 5,757,104 A | 5/1998 | Getman et al. |
| 5,759,199 A * | 6/1998 | Snell et al. ............... 607/60 |
| 5,800,478 A | 9/1998 | Chen et al. |
| 5,807,258 A | 9/1998 | Cimochowski et al. |
| 5,814,089 A | 9/1998 | Stokes et al. |
| 5,833,603 A | 11/1998 | Kovacs et al. |
| 5,861,018 A | 1/1999 | Feierbach |
| 5,891,180 A | 4/1999 | Greeninger et al. |
| 5,904,708 A * | 5/1999 | Goedeke .................. 607/18 |
| 5,925,001 A | 7/1999 | Hoyt et al. |
| 5,935,078 A | 8/1999 | Feierbach |
| 5,957,861 A | 9/1999 | Combs et al. |
| 5,967,989 A | 10/1999 | Cimochowski et al. |
| 6,015,387 A | 1/2000 | Schwartz et al. |
| 6,030,374 A | 2/2000 | McDaniel |
| 6,070,103 A | 5/2000 | Ogden |
| 6,140,740 A | 10/2000 | Porat et al. |
| 6,141,588 A | 10/2000 | Cox |
| 6,162,238 A | 12/2000 | Kaplan et al. |
| 6,164,284 A | 12/2000 | Schulman et al. |
| 6,167,303 A | 12/2000 | Thompson |
| 6,170,488 B1 | 1/2001 | Spillman, Jr. et al. |
| 6,176,840 B1 | 1/2001 | Nishimura et al. |
| 6,183,426 B1 | 2/2001 | Akisada et al. |
| 6,185,452 B1 * | 2/2001 | Schulman et al. ............. 604/20 |
| 6,185,454 B1 | 2/2001 | Thompson |
| 6,185,460 B1 | 2/2001 | Thompson |
| 6,198,963 B1 | 3/2001 | Haim et al. |
| 6,198,965 B1 | 3/2001 | Penner et al. |
| 6,198,971 B1 | 3/2001 | Leysieffer |
| 6,200,265 B1 | 3/2001 | Walsh et al. |
| 6,236,889 B1 | 5/2001 | Soykan et al. |
| 6,237,398 B1 | 5/2001 | Porat et al. |
| 6,248,080 B1 | 6/2001 | Miesel et al. |
| 6,259,951 B1 | 7/2001 | Kuzma et al. |
| 6,260,152 B1 | 7/2001 | Cole et al. |
| 6,261,249 B1 | 7/2001 | Tallish et al. |
| 6,277,078 B1 | 8/2001 | Porat et al. |
| 6,315,721 B2 | 11/2001 | Schulman et al. |
| 6,427,088 B1 | 7/2002 | Bowman et al. |
| 6,431,175 B1 | 8/2002 | Penner et al. |
| 6,432,050 B1 | 8/2002 | Porat et al. |
| 6,442,413 B1 | 8/2002 | Silver |
| 6,442,433 B1 | 8/2002 | Linberg |
| 6,472,991 B1 | 10/2002 | Schulman et al. |
| 6,473,638 B2 * | 10/2002 | Ferek-Petric ................ 600/523 |
| 6,564,807 B1 * | 5/2003 | Schulman et al. ............. 128/899 |
| 6,577,899 B2 * | 6/2003 | Lebel et al. .................. 607/60 |
| 6,584,352 B2 * | 6/2003 | Combs et al. .................... 607/9 |
| 6,607,485 B2 | 8/2003 | Bardy |
| 6,628,989 B1 | 9/2003 | Penner et al. |
| 6,644,322 B2 | 11/2003 | Webb |
| 6,664,763 B2 | 12/2003 | Echarri et al. |
| 6,671,552 B2 | 12/2003 | Merritt et al. |
| 6,676,601 B1 | 1/2004 | Lacoste |
| 6,689,091 B2 | 2/2004 | Bui et al. |
| 6,712,772 B2 | 3/2004 | Cohen et al. |
| 6,731,976 B2 | 5/2004 | Penn et al. |
| 6,735,532 B2 | 5/2004 | Freed et al. |
| 6,754,538 B2 | 6/2004 | Linberg |
| 6,764,446 B2 | 7/2004 | Wolinsky et al. |
| 6,788,973 B2 | 9/2004 | Davis et al. |
| 6,790,187 B2 | 9/2004 | Thompson et al. |
| 6,799,280 B1 | 9/2004 | Edenfield et al. |
| 6,804,557 B1 | 10/2004 | Kroll |
| 6,826,430 B2 | 11/2004 | Faltys et al. |
| 6,855,115 B2 | 2/2005 | Fonseca et al. |
| 6,873,869 B2 | 3/2005 | Fischer |
| 6,960,801 B2 | 11/2005 | Lung |
| 6,970,037 B2 | 11/2005 | Sakhuja et al. |
| 6,978,181 B1 | 12/2005 | Snell |
| 6,985,088 B2 | 1/2006 | Goetz et al. |
| 6,985,773 B2 | 1/2006 | Von Arx et al. |
| 6,988,215 B2 | 1/2006 | Splett et al. |
| 6,993,393 B2 | 1/2006 | Von Arx et al. |
| 7,003,349 B1 | 2/2006 | Andersson et al. |
| 7,013,178 B2 | 3/2006 | Reinke et al. |
| 7,024,248 B2 | 4/2006 | Penner et al. |
| 7,027,871 B2 | 4/2006 | Burnes et al. |
| 7,027,872 B2 * | 4/2006 | Thompson .................. 607/60 |
| 7,035,684 B2 | 4/2006 | Lee |
| 7,060,030 B2 | 6/2006 | Von Arx et al. |
| 7,061,381 B2 | 6/2006 | Forcier et al. |
| 7,082,334 B2 * | 7/2006 | Boute et al. .................. 607/60 |
| 7,096,068 B2 | 8/2006 | Mass et al. |
| 7,123,964 B2 | 10/2006 | Betzold et al. |
| 7,198,603 B2 | 4/2007 | Penner et al. |
| 7,203,551 B2 | 4/2007 | Houben et al. |
| 7,209,790 B2 * | 4/2007 | Thompson et al. ............. 607/60 |
| 7,212,133 B2 | 5/2007 | Goetz et al. |
| 7,236,821 B2 | 6/2007 | Cates et al. |
| 7,273,457 B2 | 9/2007 | Penner et al. |
| 7,283,874 B2 | 10/2007 | Penner et al. |
| 7,286,872 B2 | 10/2007 | Kramer et al. |
| 7,319,903 B2 | 1/2008 | Bange et al. |
| 7,335,161 B2 | 2/2008 | Von Arx et al. |
| 7,353,063 B2 * | 4/2008 | Simms, Jr. .................. 607/32 |
| 7,469,161 B1 | 12/2008 | Gandhi et al. |
| 7,479,108 B2 | 1/2009 | Rini et al. |
| 7,617,001 B2 | 11/2009 | Penner et al. |
| 7,650,185 B2 | 1/2010 | Maile et al. |
| 7,756,587 B2 | 7/2010 | Penner et al. |

| | | | |
|---|---|---|---|
| 2001/0025139 A1 | 9/2001 | Pearlman | |
| 2002/0065540 A1 | 5/2002 | Lebel et al. | |
| 2002/0077673 A1* | 6/2002 | Penner et al. | 607/60 |
| 2002/0151770 A1 | 10/2002 | Noll, III et al. | |
| 2003/0114897 A1 | 6/2003 | Von Arx et al. | |
| 2003/0212441 A1* | 11/2003 | Starkweather et al. | 607/60 |
| 2004/0039424 A1 | 2/2004 | Merritt et al. | |
| 2004/0133092 A1 | 7/2004 | Kain | |
| 2004/0152999 A1 | 8/2004 | Cohen et al. | |
| 2004/0172083 A1 | 9/2004 | Penner | |
| 2004/0210141 A1 | 10/2004 | Miller | |
| 2005/0113705 A1 | 5/2005 | Fischell et al. | |
| 2005/0159785 A1 | 7/2005 | Rueter | |
| 2005/0159789 A1* | 7/2005 | Brockway et al. | 607/32 |
| 2005/0203444 A1 | 9/2005 | Schonenberger et al. | |
| 2005/0288727 A1* | 12/2005 | Penner | 607/32 |
| 2006/0009818 A1* | 1/2006 | Von Arx et al. | 607/60 |
| 2006/0020307 A1 | 1/2006 | Davis et al. | |
| 2006/0025834 A1 | 2/2006 | Von Arx et al. | |
| 2006/0031378 A1 | 2/2006 | Vallapureddy et al. | |
| 2006/0041287 A1 | 2/2006 | Dewing et al. | |
| 2006/0041288 A1 | 2/2006 | Dewing et al. | |
| 2006/0058627 A1 | 3/2006 | Flaherty et al. | |
| 2006/0064134 A1 | 3/2006 | Mazar et al. | |
| 2006/0064135 A1 | 3/2006 | Brockway | |
| 2006/0064142 A1 | 3/2006 | Chavan et al. | |
| 2006/0085039 A1 | 4/2006 | Hastings et al. | |
| 2006/0122667 A1 | 6/2006 | Chavan et al. | |
| 2006/0142819 A1 | 6/2006 | Penner et al. | |
| 2006/0149329 A1 | 7/2006 | Penner | |
| 2007/0010742 A1 | 1/2007 | Torp et al. | |
| 2007/0142728 A1 | 6/2007 | Penner et al. | |
| 2007/0150014 A1 | 6/2007 | Kramer et al. | |
| 2007/0162090 A1 | 7/2007 | Penner | |
| 2007/0179549 A1 | 8/2007 | Russie | |
| 2007/0250126 A1 | 10/2007 | Maile et al. | |
| 2008/0015421 A1 | 1/2008 | Penner | |
| 2008/0071178 A1 | 3/2008 | Greenland et al. | |
| 2008/0103553 A1 | 5/2008 | Penner et al. | |
| 2008/0108915 A1 | 5/2008 | Penner | |
| 2008/0171941 A1 | 7/2008 | Huelskamp et al. | |
| 2008/0195002 A1 | 8/2008 | Thompson et al. | |
| 2008/0243210 A1 | 10/2008 | Doron et al. | |
| 2009/0312650 A1 | 12/2009 | Maile et al. | |
| 2009/0326609 A1 | 12/2009 | Doron | |
| 2010/0023091 A1 | 1/2010 | Stahmann et al. | |
| 2010/0106028 A1 | 4/2010 | Penner et al. | |
| 2011/0160804 A1 | 6/2011 | Penner | |

FOREIGN PATENT DOCUMENTS

| | | |
|---|---|---|
| EP | 0 928 598 | 12/1998 |
| EP | 1962557 | 8/2008 |
| JP | 10-505529 | 6/1998 |
| JP | 2004537347 | 12/2004 |
| JP | 2005521528 | 7/2005 |
| WO | WO 88/02250 | 4/1988 |
| WO | WO 9626673 A1 | 9/1996 |
| WO | WO98/43338 | 10/1998 |
| WO | WO99/34453 | 7/1999 |
| WO | WO00/47109 | 8/2000 |
| WO | WO01/28627 | 4/2001 |
| WO | WO01/74278 | 10/2001 |
| WO | WO 01/97907 A2 | 12/2001 |
| WO | WO02/03347 | 1/2002 |
| WO | WO 02/32502 | 4/2002 |
| WO | WO 02089904 A1 | 11/2002 |
| WO | WO03/002243 | 1/2003 |
| WO | WO 03/043688 | 5/2003 |
| WO | WO03/096889 | 11/2003 |
| WO | WO 2005/009535 A1 | 2/2005 |
| WO | WO 2005/053786 A2 | 6/2005 |
| WO | WO2006/060668 | 6/2006 |
| WO | WO 2007/070794 | 6/2007 |
| WO | WO2007/127696 | 11/2007 |
| WO | WO2008/118908 | 10/2008 |

OTHER PUBLICATIONS

PCT Written Opinion of the International Search Authority for PCT/IB2007/000052, Applicant: Remon Medical Technologies Ltd., Form PCT/ISA/237, dated Jun. 21, 2007 (6 pages).

Harrison et al., "A Low-Power Low-Noise CMOS Amplifier for Neural Recording Applications," IEEE Journal of Solid-State Circuits 38(6):958-965, Jun. 2003.

IEEE Transactions on Biomedical Engineering, vol. 42, No. 5, May 1995, Title: Data Transmission from an Implantable Biotelemeter by Load-Shift Keying Using Circuit Configuration Modulator, by Zhengnian Tang, Brian Smith, John H. Schild, and P. Hunter Peckham, pp. 524-528.

Ishiwara et al., "Current Status and Prospects of FET-Type Ferroelectric Memories," Journal of Semiconductor Technology and Science 1(1): 1-14, Mar. 2001.

Neurosurgery Clinics of North America vol. 4, No. 4, Oct. 1993, Hydrocephalus, Title: The Treatment of Hydrocephalus by Paul M. Kanev, MD, and T.S. Park, MD., pp. 611-619.

Neurosurgery Clinics of North America, vol. 4, No. 4, Oct. 1993, Hydrocephalus, Title: Complications in Ventricular Cerebrospinal Fluid Shunting by Jeffrey P. Blount, MD, John A. Campbell, MD, and Stephen J. Haines, MD, pp. 633-656.

Neurosurgery Update II Vascular, Spinal, Pediatric, and Functional Neurosurgery, Published by McGraw-Hill, Inc., 1991, Editors Robert H. Wilkins, M.D., and Setti S. Rengachary, M.D., Title Shunt Complications by R. Michael Scott, pp. 300-319.

Neurosurgery, vol. 34, No. 5, May 1994, Concepts and Innovations, Title: A New Ventricular Catheter for the Prevention and Treatment of Proximal Obstruction in Cerebrospinal Fluid Shunts, by Enrique C.G. Ventureyra, M.D., F.R.C.S.(C)., F.A.C.S., Michael J. Higgins, M.D., pp. 924-926.

Neurosurgery, vol. 34, No. 6, Jun. 1994, Rapid Communication, Title: The Use of the Codman-Medos Programmable Hakim Valve in the Management of Patients with Hydroceplhalus: Illustrative Cases, by Peter McL. Black, M.D., Ph.D., Rodolfo Hakim, M.D., Nancy Olsen Bailey, R.N., B.S.N., M.B.A., pp. 1110-1113.

Pediatric Neurosurgery 2nd Edition, Surgery of the Developing Nervous System, Published by W.B. Saunders Company Harcourt Brace Jovanovich, Inc., 1989. Title: Treatment of Hydrocephalus by Harold L. Rekate, M.D.; Ventricular Shunts: Complications and Results by Robert L. McLaurin, M.D.; pp. 200-229.

* cited by examiner

BODY ATTACHABLE UNIT IN WIRELESS COMMUNICATION WITH IMPLANTABLE DEVICES

RELATED APPLICATIONS

This application claims priority under the provisions of 35 U.S.C. §119(e) from U.S. Provisional Patent Application Ser. No. 60/757,712, filed Jan. 10, 2006.

BACKGROUND OF THE INVENTION

Devices are known that may be implanted within a patient's body to monitor one or more physiological conditions and/or to provide therapeutic functions. For example, sensors or transducers may be located deep within the body for monitoring a variety of properties, such as temperature, pressure, strain, fluid flow, chemical properties, electrical properties, magnetic properties, and the like. In addition, devices may be implanted that perform one or more therapeutic functions, such as drug delivery, defibrillation, electrical stimulation, and the like. Often it is desirable to control or otherwise communicate with such devices once they are implanted within a patient, for example, to obtain data, and/or to activate or deactivate the implanted device.

Various methods for activating and communicating with implants have been suggested. Most relevant to the current invention is the activation, controlling and communication with implants using acoustic energy, as described by Penner and Doron in U.S. Pat. No. 7,198,603, entitled "Apparatus and Methods Using Acoustic Telemetry for Intrabody Communications," which is expressly incorporated herein by reference. In U.S. Pat. No. 7,024,248 entitled "Systems and Methods For Communicating with Implantable Devices," which is expressly incorporated herein by reference, the same inventors described systems and methods for communicating with an implant within a patient's body using acoustic telemetry based on an external communications device attachable to the patient's skin. Significantly, because other forms of energy, such as radio frequency (RF) energy, can only penetrate a few millimeters into a body due to the dielectric nature of tissue, wirelessly communicating using acoustic energy, which does not significantly attenuate when traveling through tissue, lends itself well to implementations where it is desirable to communicate with a device that has been implanted deep within the tissue.

It is sometimes desirable to wirelessly communicate between implanted devices. For example, U.S. Patent Publication No. 2005/0288727, entitled "Wireless Sensing Devices for Evaluating Heart Performance," which is expressly incorporated herein by reference, describes a system for evaluating the performance and status of a heart and optionally providing therapy to the heart based on the evaluation. In this exemplary system, diagnostic devices, such as accelerometers, strain gauges, or tactile sensors, are implanted within various locations of the heart to measure certain characteristics of the heart, e.g., contractility or movement. One or more therapeutic devices, such as a drug pump, implantable pulse generator (IPG) (e.g., pacemaker, implantable cardioverter defibrillator (ICD), or cardiac resynchronization therapy (CRT) device, such as a CRT-P (pacemaker) or CRT-D (defibrillator)), or nerve simulator, can be implanted within the appropriate region of the body. The operation of the therapeutic device(s) may then be controlled or optimized based on the information received from the diagnostic devices.

While direct wireless communication between implanted devices works in theory, this implementation has drawbacks. For example, to enable direct wireless communication between two implantable devices, both devices should have the same means of communication, e.g., both should either wirelessly communicate acoustically or wirelessly communicate electromagnetically. Thus, in the case where it is desirable that the diagnostic device be equipped with an acoustic means of communication, e.g., if it is to be implanted deep with the patient's body, than a therapeutic device that directly communicates with the diagnostic device should likewise be equipped with a similar acoustic means of communications. However, this requires a significant modification to existing therapeutic devices (which oftentimes use electromagnetic energy to wirelessly communicate), including modification of an on-board integrated circuit (IC) and software, incorporation of an acoustic transducer, and several other changes. Such changes will lead to an increase in the size and energy consumption of the therapeutic device, as well as the need to revalidate the therapeutic device—a tedious task that the manufacturer/distributor of the therapeutic device would rather avoid.

There thus is a need to provide an improved system that allows two or more implantable devices to interact with each other.

SUMMARY OF THE INVENTION

The present inventions are directed to medical systems that include implantable devices and an external device configured for wirelessly interacting with the implantable devices. In accordance with a first aspect of the present invention, the external device is attachable to a patient and is configured for wirelessly receiving information from a first implantable device, and wirelessly interacting with a second implantable device based on the information received from the first implantable device. In accordance with a separate second aspect of the present inventions, the first implantable device is an implantable diagnostic device, the second implantable device is an implantable therapeutic device, and the external device is configured for wirelessly acquiring physiological information from the implantable diagnostic device, and for wirelessly interacting with the implantable therapeutic device to provide therapy to the patient. In accordance with a separate third aspect of the present inventions, the external device is configured for wirelessly interacting with the first implantable device using acoustic energy, and wirelessly interacting with the second implantable device using non-acoustic energy.

While the present inventions should not be so limited in their broadest aspects, the use of an external device obviates the need for the implantable devices to communicate or interact directly with each other. In the case where acoustic energy is used to wirelessly interact with the first implantable device, and non-acoustic energy is used to wirelessly interact with the second implantable device, the first device may be implanted deeply within the tissue of the patient, and the second device can take the form of standard devices that currently use electromagnetic or magnetic means to wirelessly communicate.

In the case where the first implantable device is an implantable diagnostic device, the second implantable device is an implantable therapeutic device, and the external device wirelessly receives the physiological information from the diagnostic device, the external device may wirelessly interact with the therapeutic device in a variety of manners to optimize therapy provided to the patient. For example, the external device may wirelessly transmit therapeutic optimization information to the therapeutic device and/or actually control the therapeutic device.

In this case where therapeutic optimization information is wirelessly transmitted from the external device to the therapeutic device, the therapeutic optimization information may comprise the physiological information received from the diagnostic device, and the therapeutic device may derive one or more therapeutic optimization parameters from the physiological information. Or the external device may derive the therapeutic optimization parameter(s) from the physiological information received from the diagnostic device, and wirelessly transmit the therapeutic optimization parameter(s) as the therapeutic optimization information to the therapeutic device.

The present inventions are also directed to medical devices that may function as the external device in the medical systems described above. The medical device comprises one or more wireless transducers (e.g., an acoustic transducer and a non-acoustic transducer, such as an electromagnetic or magnetic antenna), a control/processing unit coupled to the wireless transducer(s) for wirelessly interacting with first and second implanted devices in the manner described above with respect to the medical systems, and a casing for carrying the transducer(s) and control/processing unit. If the medical device is to be attached to a patient, it can comprise a mechanism configured for externally attaching the casing to the patient, e.g., a strap, belt, patch, etc., thereby operably coupling the acoustic transducer to the patient's body, thereby facilitating wireless communication with any acoustic device implanted deeply within the patient's tissue.

Other and further aspects and features of the invention will be evident from reading the following detailed description of the preferred embodiments, which are intended to illustrate, not limit, the invention.

BRIEF DESCRIPTION OF THE DRAWINGS

The drawings illustrate the design and utility of preferred embodiments of the present invention, in which similar elements are referred to by common reference numerals. In order to better appreciate how the above-recited and other advantages of the present inventions are obtained, a more particular description of the present inventions briefly described above will be rendered by reference to specific embodiments thereof, which are illustrated in the accompanying drawings. Understanding that these drawings depict only typical embodiments of the invention and are not therefore to be considered limiting of its scope, the invention will be described and explained with additional specificity and detail through the use of the accompanying drawings in which.

DETAILED DESCRIPTION OF EMBODIMENTS

Figure 1:
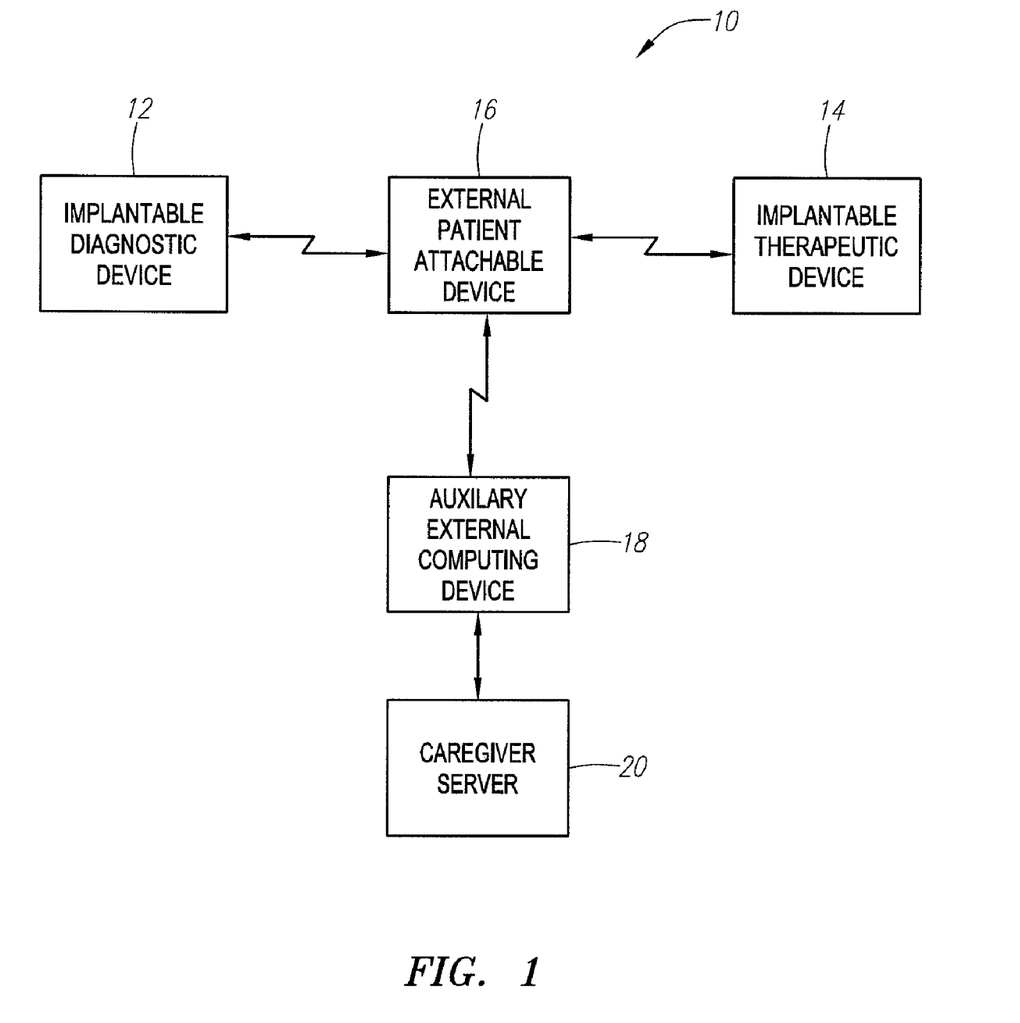
FIG. 1 is a block diagram of an implantable system constructed in accordance with one embodiment of the present inventions.

Referring to FIG. 1, an implantable system 10 constructed in accordance with one embodiment of the present inventions will now be described. The implantable system 10 generally comprises an implantable diagnostic device 12, which is configured for acquiring physiological information from a patient, an implantable therapeutic device 14, which is configured for providing therapy to the patient, and an external attachable device 16 at least partially in contact with the patient's body. The patient attachable device 16 is configured for wirelessly interacting with, and providing an intermediary between, the diagnostic device 12 and the therapeutic device 14.

In the illustrated embodiment, the patient attachable device 16 is configured for wirelessly communicating with the diagnostic device 12, and wirelessly interacting with the implantable therapeutic device 14 based on the communication with the diagnostic device 12. For example, the patient attachable device 16 may wirelessly receive physiological information from the diagnostic device 12, and wirelessly transmit therapeutic optimization information (e.g., the physiological information itself, and/or additional physiological information, and/or therapeutic optimization parameters for optimizing the therapeutic protocol) to the therapeutic device 14 to optimize the therapy provided to the patient and/or control the therapeutic device 14 to provide the therapy to the patient. For example, a particular course of treatment for the patient may be determined, such as a flow rate and duration of drug delivery or an energy level and duration of electrical stimulation. In the illustrated embodiment, the diagnostic device 12 remains in a "dormant state" until awoken to an "active state" by the patient attachable device 16, while the therapeutic device 14 is always in an "active state."

As illustrated in FIG. 1, the implantable system 10 further comprises an optional external auxiliary computing device 18, e.g., a desktop or portable computer, and a caregiver server or database 20. The auxiliary computing device 18 is in wireless communication with the patient attachable device 16 and may be connected to the caregiver server 20 via the Internet or other communications means, such as a phone line or cell phone. The auxiliary computing device 18 may be used to provide additional computing power and storage capability to the implantable system 10, provide measurements, and to provide an intermediary between the patient attachable device 16 and the caregiver server 20 to provide notification information to the caregiver server 20, and acquire additional information from the caregiver server 20 if needed. The auxiliary computing device 18 can generate command signals, or receive command signals from the caregiver server 20, which command signals can then be wirelessly transmitted to the patient attachable device 16. The auxiliary computing device 18 can also be used to wirelessly transmit information to the therapeutic device 14.

Figure 2:
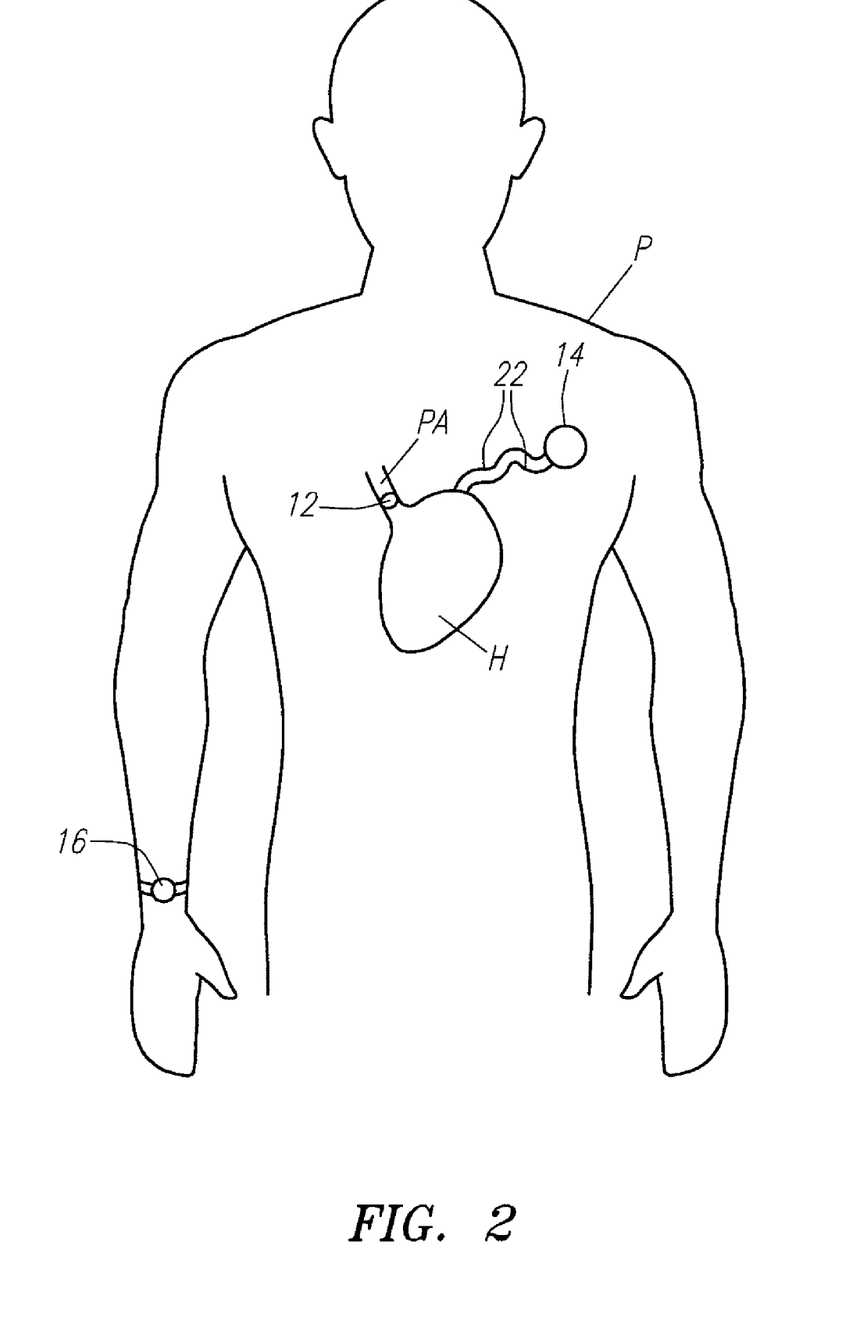
FIG. 2 is a schematic view of the implantable system of FIG. 1 arranged on a patient's body.

As illustrated in FIG. 2, the implantable system 10 can be used to acquire physiological information indicative of the status of a heart H and provide therapy to the heart H based on the acquired physiological information. To this end, the diagnostic device 12 and therapeutic device 14 are implanted within or adjacent to the heart H. For example, the diagnostic device 12 is illustrated as being implanted within a pulmonary artery PA for measuring one or more physiological parameters therein, and the therapeutic device 14 is illustrated as being implanted under the skin of the patient's chest for providing therapy to the heart H.

In one embodiment, the measured physiological parameters include an absolute pressure within the heart H or pulmonary artery PA, in which case, the diagnostic device 12 may take the form of a pressure sensor. While the diagnostic device 12 is shown as being located in the pulmonary artery PA where absolute pressure correlated to the heart can be measured, the diagnostic device 12 can be located in other regions where the absolute pressure can be measured, e.g., the heart septum or a heart chamber, e.g., the left ventricle. Alternatively, other physiological parameters that can only be measured in or around the heart H, such as strain or movement of the heart wall, electrical activity, electrical impedance, etc., may be measured by the diagnostic device 12. Additional diagnostic devices may be implanted within or adjacent the heart H if needed.

In the illustrated embodiment, the therapeutic device 14 takes the form of an electrical stimulation device, such as an Implantable Pulse Generator (IPG) (e.g., a pace maker, Implantable Cardioverter Defibrillator (ICD), or a Cardiac Resynchronization therapy (CRT) device), that is functionally coupled to the heart H via wires 22. In another preferred embodiment, the IPG may take the form of a nerve stimulator, or the therapeutic device 14 may take the form of a non-IPG therapeutic device, such as a drug pump. The therapeutic device 14 may optionally include sensors to measure physiological parameters not otherwise measured by the diagnostic device 12, e.g., heart rate, temperature, posture, etc., and use this information to optimize therapy separately or in conjunction with the diagnostic information measured by the diagnostic device 12.

As briefly discussed above, the patient attachable device 16 operates as an intermediary between the diagnostic device 12 and therapeutic device 14 by wirelessly receiving the physiological information from the diagnostic device 12 and wirelessly transmitting therapeutic optimization information to the therapeutic device 14, thereby facilitating optimization of the therapy provided to the patient.

For example, the patient attachable device 16 can transmit the physiological information received from the diagnostic device 12 to the therapeutic device 14, which then derives therapeutic optimization parameters from this therapeutic optimization information. These therapeutic optimization parameters can then be used by the therapeutic device 14 to modify a pre-programmed protocol used to provide the therapy. In the case where the physiological information includes absolute pressure, the patient attachable device 16 may also transmit a barometric pressure, which may be measured by the patient attachable device 16 or the auxiliary external computing device 18, to the therapeutic device 14, such that a gauge pressure may be calculated as a function of the barometric pressure and the absolute pressure. Alternatively, rather than wirelessly transmitting the physiological information or other measured information (e.g., the absolute pressure and barometric pressure), the patient attachable device 16 may derive the therapeutic optimization parameters from the physiological information, and wirelessly transmit the therapeutic optimization parameters to the therapeutic device 14. Alternatively, rather than the therapeutic device 14 or patient attachable device 16 deriving the therapeutic optimization parameters, the auxiliary external computing device 18 or even the caregiver server 20 may derive and transmit the therapeutic optimization parameters to the therapeutic device 14 via the patient attachable device 16.

By way of non-limiting example, the measurement of absolute pressure in the heart and surrounding anatomical structures may be useful in the treatment of the patient in several ways. For a congestive heart failure (CHF) patient, the measurement of left ventricle end diastolic pressure, or a surrogate thereof, may help in the evaluation of the patient's heart status and facilitate the optimization of drug therapy, in which case, the therapeutic device 14 may be a drug pump implanted within the patient. Based on the measured diastolic pressure, the optimal titration of a diuretic released by the drug pump can be achieved to maintain the patient between dry state (reduced amount of body fluids including blood volume) and wet state, which may lead to edema (accumulation of fluids in the lungs). Notably, lung edema is the main cause of hospitalization for CHF patients and the leading cause of the death for these patients. The measurement of diastolic pressure can also help in detecting ischemia in a patient suffering from a heart ailment.

The measurement of diastolic pressure within the heart can also be used to optimize electrical stimulation therapy, in which case, the therapeutic device 14 may take the form of an electrical stimulation device. For example, diastolic pressure measurements can be used to automatically close a therapeutic cycle and optimize the parameters of an IPG as a function of pressure (hemodynamic feedback). Diastolic pressure measurements may be used to substantially reduce the number of unnecessary shocks (approximately 50% of shocks are unnecessary) generated by an ICD. Diastolic pressure measurements may be used to dynamically modify the operation of a CRT device by optimizing the delay between the left and right ventricle stimulation, thereby synchronizing ventricle contraction.

Because the diagnostic device 12 is implanted deep within the tissue of the patient, and in particular the heart or adjacent anatomical structures, preferably, the patient attachable device 16 wirelessly communicates with the diagnostic device 12 using acoustic energy (e.g., at a relatively low frequency of 40 KHz), and in particular, by transmitting and receiving acoustic energy through the tissue. Thus, the patient attachable device 16 may wirelessly receive the physiological information from the diagnostic device 12 using acoustic energy. The patient attachable device 16 may also transmit acoustic energy to control or operate the diagnostic device 12. For example, the patient attachable device 16 may activate and deactivate the diagnostic device 12 (i.e., alternately placing it in an "active mode" and "dormant mode"). The patient attachable device 16 may also transmit acoustic energy to charge the diagnostic device 12.

To this end, the patient attachable device 16 is placed in close contact with the patient's skin. By way of non-limiting example, the attachable device 16 is illustrated in FIG. 2 as being attached to the patient's wrist using a wrist band type attachment mechanism. Alternatively, the attachable device 16 can be attached to any other part of the patient's body, such as the arm, neck, chest, thigh, and knee. The attachable device 16 can use any type of attachment mechanism, such as a strap, a patch, a belt, or any other means for assuring contact between at least part of the acoustically active component of the attachable device 16 and the patient's body. Further details regarding various means of securely attaching control devices to patients are provided in U.S. patent application Ser. No. 10/632,265, which is expressly incorporated herein by reference.

Due largely to the superficial implantation of the therapeutic device 14 within the patient's chest, e.g., just under the skin, the patient attachable device 16 may wirelessly communicate with the therapeutic device 14 using non-acoustic energy, such as electromagnetic (e.g., radio frequency (RF)) or magnetic energy. Thus, in addition to obviating the need to provide direct communication between the diagnostic device 12 and therapeutic device 14, standard therapeutic devices that utilize current electromagnetic technology for wireless communication (e.g., Bluetooth RF technology) can be incorporated into the system 10 without significant modification.

Figure 3:
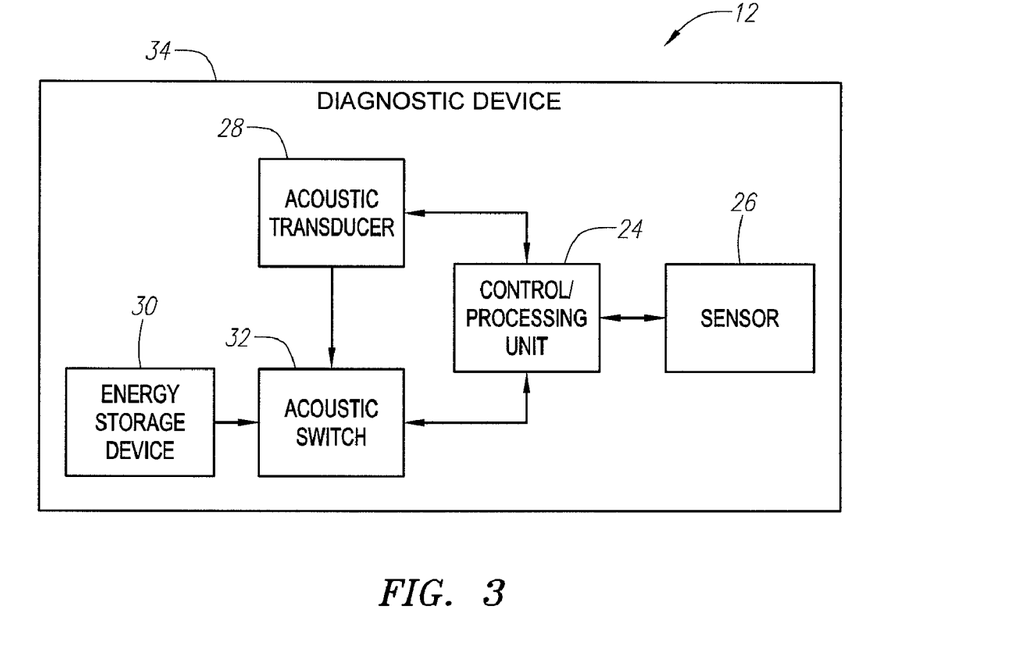
FIG. 3 is a block diagram of an implantable diagnostic device used in the implantable system of FIG. 1.

Turning now to FIG. 3, the structure of the diagnostic device 12 will be described. The diagnostic device 12 comprises a plurality of components, including a control/processing unit 24, sensor 26, acoustic transducer 28, energy storage device 30, and acoustic switch 32, housed within a casing 34. The casing 34 is composed of a suitable biocompatible material and is hermetically sealed to isolate the components from the environment outside of the diagnostic device 12. Further details regarding the construction of casings for implantable devices are described in U.S. Pat. No. 6,764,446, which is expressly incorporated herein by reference.

The sensor 26 may be any desired biosensor that generates a signal proportional to a measured physiological parameter that may be processed and wirelessly transmitted from the control/processing unit 24 to the patient attachable device 16 via the acoustic transducer 28. Such physiological parameters may include pressure, temperature, electrical impedance, position, strain, pH, blood flow, and the like. Additional sensors may be provided if the measurement of additional physiological parameters is desired. Under control of the control/processing unit 22, the physiological parameters may be measured and the resulting physiological information transmitted from the diagnostic device 12 continuously or periodically until the diagnostic device 12 is deactivated, or for a fixed predetermined time, as will be appreciated by those skilled in the art.

The acoustic transducer 28 includes one or more piezoelectric elements configured for transmitting and receiving acoustic signals. In particular, the acoustic transducer 28 generates an electrical signal proportional to the magnitude of acoustic energy received by the acoustic transducer 28, which electrical signal is conveyed to the control/processing unit 24. Similarly, the acoustic transducer 28 generates an acoustic signal proportional to the magnitude of the electrical energy conveyed from the control/processing unit 24 to the acoustic transducer 28. Further details regarding the construction of acoustic transducers for implantable devices are described in U.S. Pat. No. 6,140,740, which is expressly incorporated herein by reference.

The energy storage device 30 may be any of a variety of known devices, such as an energy exchanger, a battery and/or a capacitor. Preferably, the energy storage device 30 is capable of storing electrical energy substantially indefinitely unless actively discharged. In addition, the energy storage device 30 may be capable of being charged from an external source, and in particular, from acoustic energy transmitted to the diagnostic device 12 from the patient attachable unit 16.

The acoustic switch 32 is activated upon acoustic excitation of the acoustic transducer 28 by an acoustic activation signal transmitted by the patient attachable device 16 to allow current flow from the energy storage device 30 to the control/processing unit 24. Thus, the acoustic switch 32 allows the diagnostic device 12 to operate in two modes, a "sleep" or "dormant" mode when the diagnostic device 12 is not in use, i.e., when the acoustic switch 32 is open and no electrical energy is delivered from the energy storage device 30 to the control/processing unit 24, and an "active" mode, when the acoustic switch 32 is closed and electrical energy is delivered from the energy storage device 30 to the control/processing unit 24. Further details regarding the construction and function of acoustic switches are disclosed in U.S. Pat. No. 6,628,989, which is expressly incorporated herein by reference.

The control/processing unit 24 may include circuitry for activating or controlling the sensor 26 and for receiving signals from the sensor 26. The control/processing unit 24 may also include memory for storing information, e.g., data received from the sensor 26, and/or commands for use internally. The control/processing unit 24 may include an oscillator or other circuitry for wirelessly transmitting acoustic signals to the patient attachable device 16 via the acoustic transducer 28, signal detection circuitry for wirelessly receiving acoustic signals from the patient attachable device 16 via the acoustic transducer 28, and/or a processor for analyzing, interpreting, and/or processing the received signals. The control/processing unit 44 may include a processor for analyzing, interpreting, and/or processing the signals received by the sensor 26 and patient attachable device 16, and memory for storing the processed information and/or commands for use internally. The control/processing unit 24 may be configured as a digital signal processor (DSP), field programmable gate array (FPGA), application specific integrated circuit (ASIC)-compatible device, such as a CoolRISC processor available from Xemics, or other programmable devices, and/or any other hardware components or software modules that may be required for processing, analyzing, storing data, and controlling operation of the diagnostic device 12.

Figure 4:
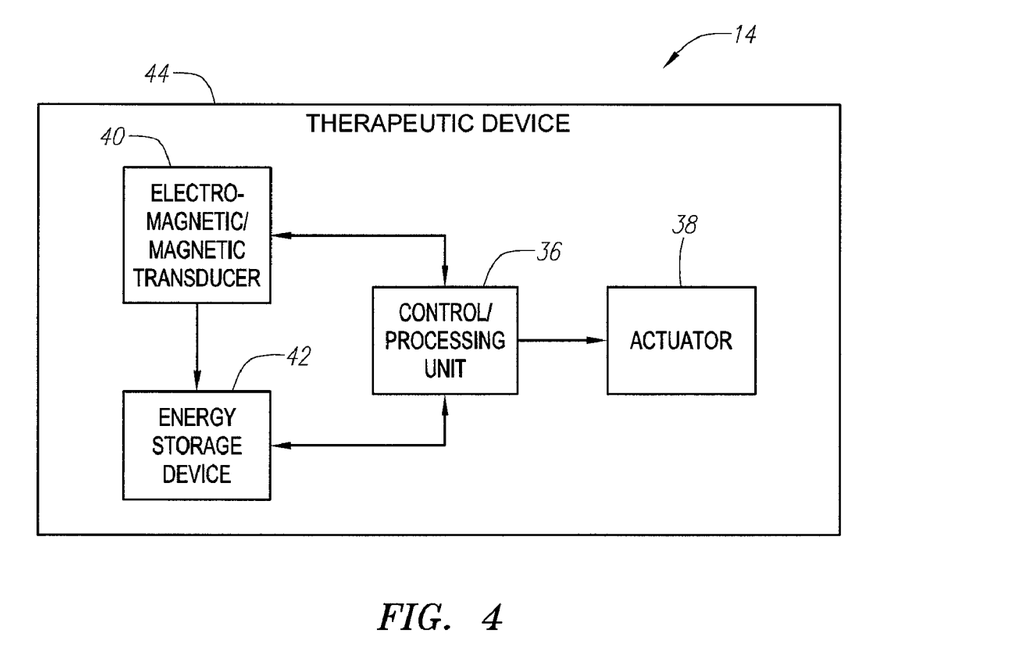
FIG. 4 is a block diagram of an implantable therapeutic device used in the implantable system of FIG. 1.

Turning now to FIG. 4, the structure of the therapeutic device 14 will be described. The therapeutic device 14 may be similar to any standard wireless-enabled therapeutic device that is currently on the market. The therapeutic device 14 comprises a plurality of components, including a control/processing unit 36, actuator 38, electromagnetic or magnetic transducer 40 (i.e., an antenna), and energy storage device 42 housed within a casing 44. The casing 44 is composed of a suitable biocompatible material and is hermetically sealed to isolate the components from the environment outside of the therapeutic device 14.

The actuator 38 may be any desired bioactuator that provides therapy to the patient, e.g., a drug pump or electrical stimulator. Additional actuators may be provided if other modes of therapy are desired. Under control of the control/processing unit 36, the actuator 38 may provide therapy continuously or periodically, or for a fixed predetermined time, as will be appreciated by those skilled in the art.

The antenna 40 may take the form of a standard antenna for transmitting and receiving electromagnetic energy in the radio frequency (RF) spectrum or pulsed magnetic energy. In particular, the antenna 40 generates an electrical signal proportional to the magnitude of electromagnetic/magnetic energy received by the antenna 40, which electrical signal is conveyed to the control/processing unit 36. Similarly, the antenna 40 generates an electromagnetic/magnetic signal proportional to the magnitude of the electrical energy conveyed from the control/processing unit 36 to the antenna 40.

The energy storage device 42 may be any of a variety of known devices, such as an energy exchanger, a battery and/or a capacitor. Preferably, the energy storage device 42 is capable of storing electrical energy substantially indefinitely unless actively discharged. In addition, the energy storage device 42 may be capable of being charged from an external source, and in particular, from acoustic energy transmitted to the diagnostic device 12 from the patient attachable unit 16. In the illustrated embodiment, the therapeutic device 14 is always active, and therefore, does not need a switch between the energy storage device 42 and the control/processing unit 36.

The control/processing unit 36 may include circuitry for activating or controlling the actuator 38. For example, the control/processing unit 36 may activate the actuator 38 using a pre-programmed protocol. The control/processing unit 36 may include an oscillator or other circuitry for wirelessly transmitting electromagnetic/magnetic signals to the patient attachable device 16 via the antenna 40, signal detection circuitry for wirelessly receiving electromagnetic/magnetic signals from the patient attachable device 16 and/or the auxiliary computing device 18 via the antenna 40, and/or a processor for analyzing, interpreting, and/or processing the received signals, and memory for storing the processed information and/or commands for use internally. The control/processing unit 36 may be configured as a digital signal processor (DSP), field programmable gate array (FPGA), application specific integrated circuit (ASIC)-compatible device, such as a CoolRISC processor available from Xemics, or other programmable devices, and/or any other hardware components or software modules that may be required for processing, analyzing, storing data, and controlling operation of the therapeutic device 14.

Figure 5:
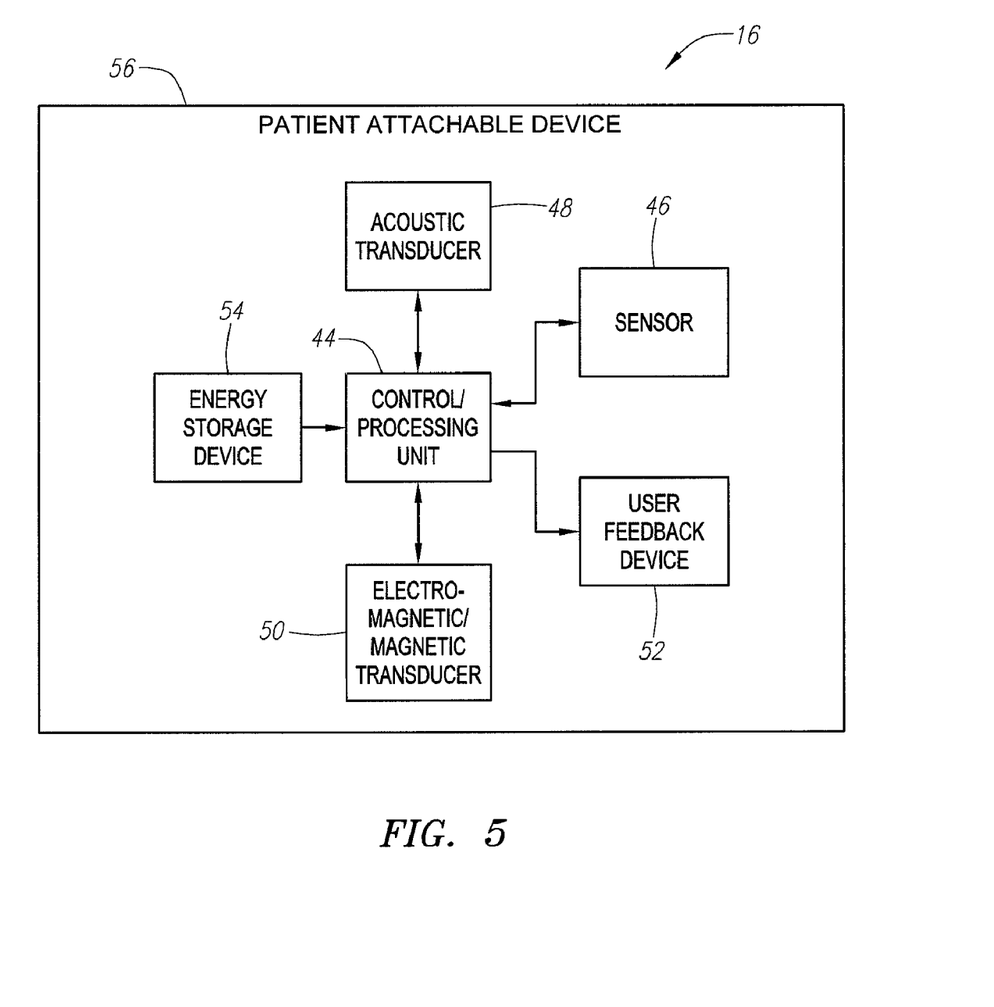
FIG. 5 is a block diagram of an external patient attachable unit used in the implantable system of FIG. 1.

Referring to FIG. 5, the patient attachable device 16 is preferably a small portable, battery operated device. The patient attachable device 16 comprises a plurality of components, including a control/processing unit 44, an optional on-board sensor 46, acoustic transducer 48, electromagnetic or magnetic transducer 50 (i.e., an antenna), audio/visual feedback means 52, and energy storage device 54, housed within a casing 56.

The sensor 46 may be any desired sensor that generates a signal proportional to a measured parameter, e.g., a barometer. The attachable device 16 may include one or more additional sensors (not shown), such as an ECG, a systemic blood pressure sensor, a posture sensor, a global positioning sensor (GPS), an activity sensor, a temperature sensor, a timer and/or an oximeter.

The acoustic transducer 48 is similar to the acoustic transducer 28 in the diagnostic device 12 in that it is configured for transmitting and receiving acoustic signals. In particular, the acoustic transducer 48 generates an electrical signal proportional to the magnitude of acoustic energy received by the acoustic transducer 48, which electrical signal is conveyed to the control/processing unit 44. Similarly, the acoustic transducer 48 generates an acoustic signal proportional to the magnitude of acoustic energy received by the acoustic transducer 48, which electrical signal is conveyed to the control/processing unit 44. Similarly, the acoustic transducer 48 generates an acoustic signal proportional to the magnitude of the electrical energy conveyed from the control/processing unit 44 to the acoustic transducer 48. Further details regarding the structure of acoustic transducers that can be used in small profile external units are disclosed in U.S. Patent Publication No. 2006/0149329, entitled "Implantable Medical Device with Integrated Acoustic Transducer," which is expressly incorporated herein by reference. The antenna 50 is similar to the antenna 40 in the therapeutic device 14 in that it is configured for transmitting and receiving electromagnetic energy in the radio frequency (RF) spectrum or pulsed magnetic energy. In particular, the antenna 50 generates an electrical signal proportional to the magnitude of electromagnetic/magnetic energy received by the antenna 50, which electrical signal is conveyed to the control/processing unit 44. Similarly, the antenna 50 generates an electromagnetic/magnetic signal proportional to the magnitude of the electrical energy conveyed from the control/processing unit 44 to the antenna 50.

The user feedback device 52 may take the form of a screen for presenting a reading from the diagnostic device 12 or on-board sensor 46 (for example, pressure reading) to the patient, and/or a speaker, and or tactile feedback means. The energy storage device 54 may be any of a variety of known devices, such as an energy exchanger, a battery and/or a capacitor. The attachable device 16 may optionally have built-in means (not shown) for connecting to the internet or via cell phone for sending information and/or means for connecting a wire to the attachable device 16 for downloading or uploading information and programs, as well as debugging and upgrading. This connection may also be used for charging the energy storage device 54.

The control/processing unit 44 may include circuitry for activating or controlling the sensor 46 and for receiving signals from the sensor 46. The control/processing unit 44 may include an oscillator or other circuitry for wirelessly transmitting acoustic signals to the diagnostic device 12 via the acoustic transducer 48, and for wirelessly transmitting electromagnetic/magnetic signals to the therapeutic device 14 and/or auxiliary computing device 18 via the antenna 50. The control/processing unit 44 may also include signal detection circuitry for wirelessly receiving acoustic signals from the diagnostic device 12 via the acoustic transducer 48, and for wirelessly receiving electromagnetic/magnetic signals from the therapeutic device 14 and/or auxiliary computing device 18 via the antenna 50. The control/processing unit 44 may include a processor for analyzing, interpreting, and/or processing the received signals, and memory for storing the processed information and/or commands for use internally. The control/processing unit 44 may be configured as a digital signal processor (DSP), field programmable gate array (FPGA), application specific integrated circuit (ASIC)-compatible device, such as a CoolRISC processor available from Xemics, or other programmable devices, and/or any other hardware components or software modules that may be required for processing, analyzing, storing data, and controlling operation of the patient attachable device 16.

Figure 6:
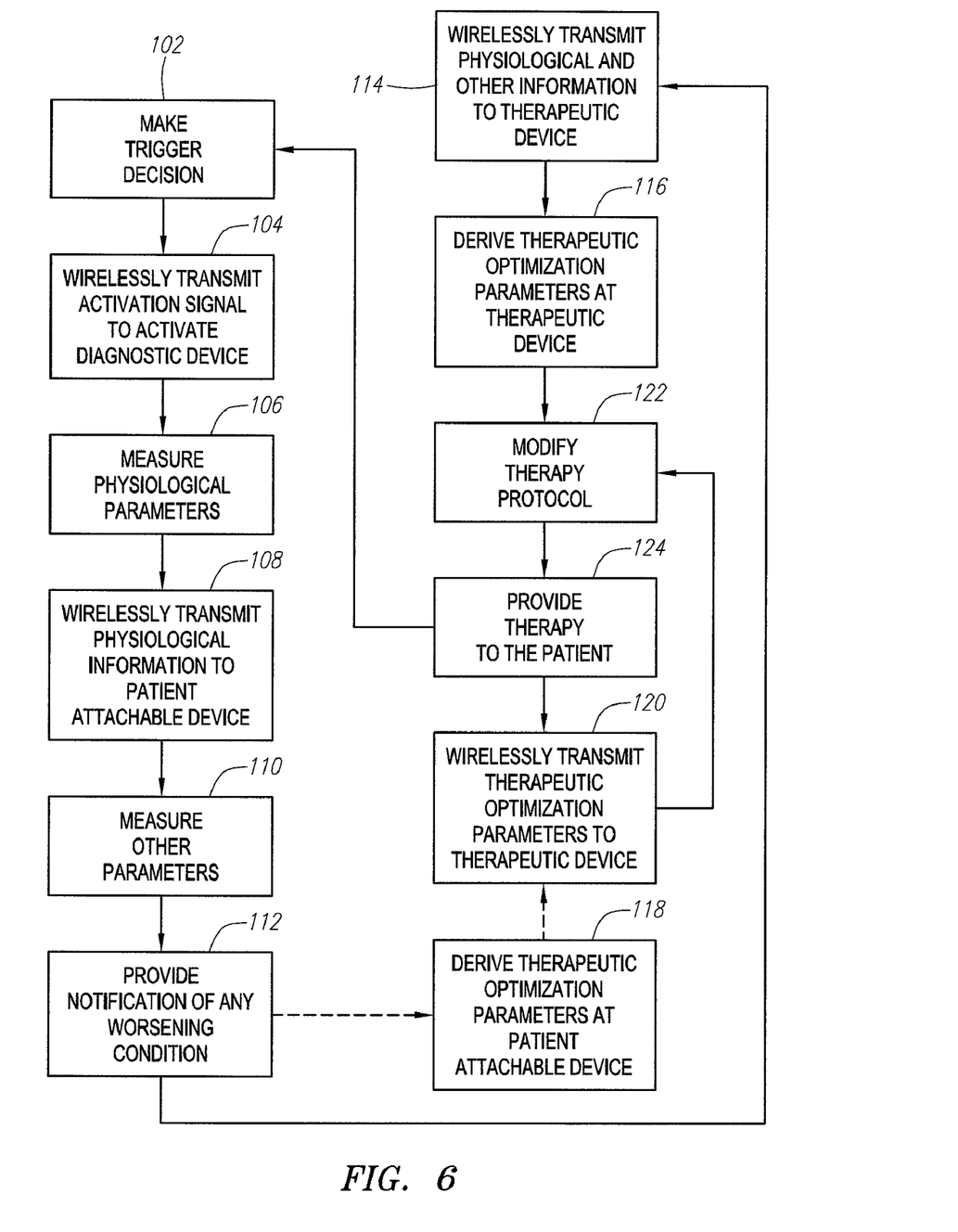
FIG. 6 is a flow chart describing the steps performed by the implantable system of FIG. 1.

Referring now to FIG. 6, one process performed by the implantable system 10 will be described. The process may be initiated in response to a trigger decision, such as a scheduled measurement (say twice a day at specific times), or a patient event, such as a specific posture of the patient, specific activity of the patient, a bio-electrical event (such as an irregular heart beat or ECG), etc. (step 102).

In one embodiment, the auxiliary computing device 18 makes the trigger decision and wirelessly transmits a trigger command signal to the patient attachable device 16 to initiate the process. In this case, the auxiliary computing device 18 may make the trigger decision based on information wirelessly received by the auxiliary computing device 18 from the therapeutic device 14, attachable device 16, or any other source.

In another embodiment, the therapeutic device 14 makes the trigger decision and wirelessly transmits a trigger command signal to the patient attachable device 16 to initiate the process. In this case, the therapeutic device 14 may make the trigger decision based on information measured by the therapeutic device 14 or deduced by it based on its measurements and/or information wirelessly transmitted to it from other sources, such as the patient attachable device 16.

In still another embodiment, the patient attachable device 16 makes the trigger decision, in which case, no trigger command signal need be transmitted to the attachable device 16. The attachable device 16 may make the trigger decision based on information measured by the patient attachable unit 16 or deduced by it based on its measurements and/or information wirelessly transmitted to it from other sources, such as the therapeutic device 14.

After a trigger decision has been made, the attached device 16 wirelessly transmits an activation command to the dormant implantable diagnostic device 16 (step 104), which then wakes up and measures physiological parameters of the patient, e.g., measuring absolute pressure within the patient's body (step 106). The diagnostic device 12 then wirelessly transmits the corresponding physiological information to the patient attachable device 16, where it may be stored in internal memory (step 108). The patient attachable device 16 may measure other parameters (e.g., barometric pressure), or alternatively, wirelessly receive the barometric pressure information from the auxiliary computing device 18 (step 110).

Based on the physiological and other information, the patient can optionally be notified on the worsening or the possible worsening of his or her status (step 112). The indication can be given separately, or in parallel, by each of the system components, e.g., the patient attachable device 16 using audible, visual, or vibration notification, or by the therapeutic device 14 via audible notification, or by the auxiliary computing device 18 via visual or audible notification. Alternatively, the physiological and other information can be wirelessly transmitted from the patient attachable device 16 to the auxiliary computing device 18, which can be relayed to the caregiver server 20, where the caregiver may be notified.

Next, the patient attachable device 16 wirelessly transmits the physiological information and other measured information (whether raw or processed) as therapeutic optimization information to the therapeutic device 14 (step 114). Alternatively, the therapeutic optimization information can be wirelessly transmitted from the patient attachable device 16 to the auxiliary computing device 18, and then from the auxiliary computing device 18 to the therapeutic device 14. Based on the received physiological information and other measured information, the implantable therapy device 14 derives therapeutic optimization parameters that can be used to optimize the therapy given to the patient by the therapeutic device 14 (step 116).

Alternatively, the patient attachable device 16 or auxiliary computing device 18 may derive the therapeutic optimization parameters from the physiological information and other measured information (step 118), and wirelessly transmit the therapeutic optimization parameters to the therapeutic device 14 (step 120). Alternatively, optimal therapy can be determined by a caregiver 120 based at least partially on measured physiological parameters transferred to it by the patient attachable device 16 via the auxiliary computing device 18. Therapeutic optimization parameters are then transferred from the caregiver 120 to the auxiliary computing device 18, which wirelessly transmits the optimization parameters to the therapeutic device 14 directly or indirectly via the patient attachable unit 16.

The therapeutic device 14 then uses the therapeutic optimization parameters (whether derived by the therapeutic device 14 or the patient attachable device 16/auxiliary computing device 18) to optimize the pre-programmed protocol (step 122). The therapeutic device 14 then provides therapy to the patient in accordance with the optimized protocol (step 124). After the therapy has been provided, the process returns to step 102 where another trigger decision is made.

Figure 7:
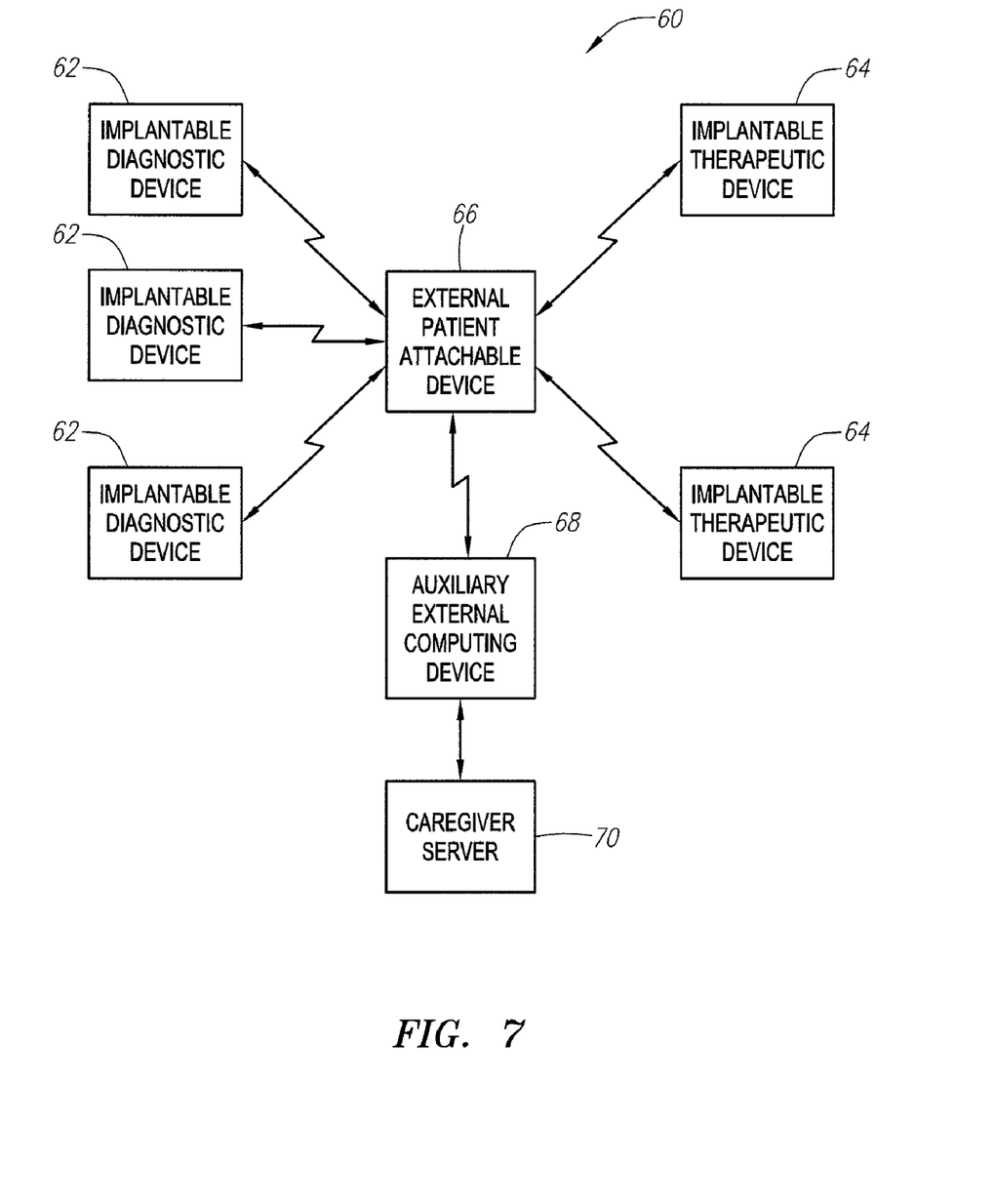
FIG. 7 is a block diagram of an implantable system constructed in accordance with another embodiment of the present inventions.
Figure 8:
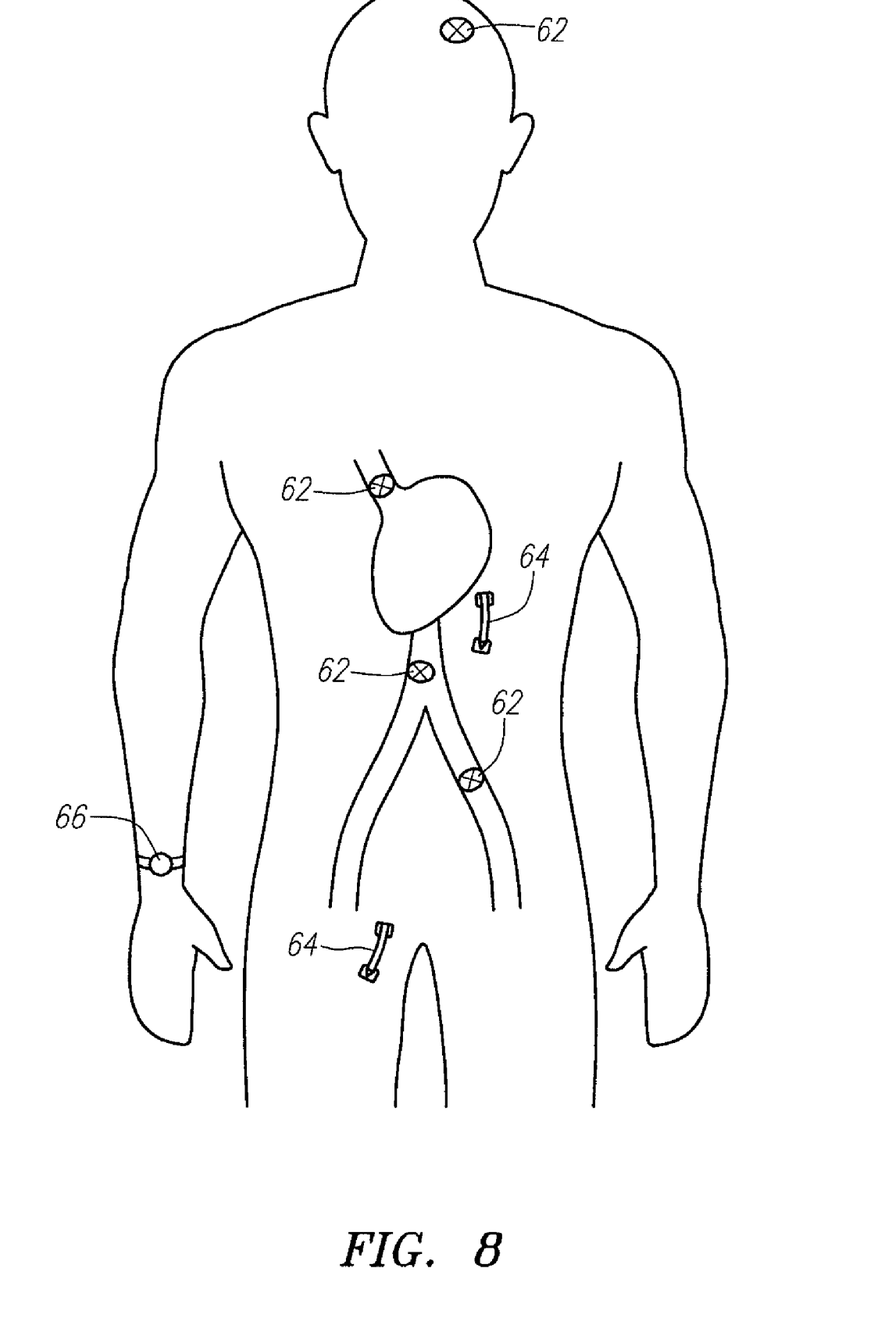
FIG. 8 is a schematic view of the implantable system of FIG. 7 arranged on a patient's body.

Referring to FIGS. 7 and 8, an implantable system 60 constructed in accordance with one embodiment of the present inventions will now be described. The implantable system 60 is similar to the previous implantable system 10, with the exception that it includes additional implantable diagnostic devices 62 and/or therapeutic devices 64. The additional implantable devices 62/64 may measure different physiological parameters or perform different functions, such as nerve stimulation or control drug release. The implantable system 60 further comprises a patient attachable device 66 that may selectively wirelessly activate each of the implantable devices 64 or groups thereof using non-acoustic energy (e.g., electromagnetic or magnetic energy) based on physiological information wirelessly received from the implantable diagnostic devices 62 using acoustic energy. The patient attachable device 66 may distinguish the implantable devices 62/64 using different activation frequencies or different identification codes. The patient attachable device 66 may activate several therapeutic devices 64 at specific pre-programmed delays or based on a feedback loop closed by the physiological information wirelessly received from the diagnostic devices 62. As an example, the patient attachable device 16 may control paralyzed organ movement by activating implantable neurostimulators at pre-programmed delays or based on a feedback loop from a sensor that monitors the organ movement. As illustrated in FIG. 7, the implantable system 60 may optionally include an auxiliary external computing device 68 and caregiver server 70 that may function and interact with the patient attachable device 66 and therapeutic device 64 in the same manner as the previously described auxiliary computing device 18 and caregiver server 20 function and interact with the patient attachable device 16 and therapeutic device 14.

While the previous embodiments contemplate that the patient attachable device wirelessly receives physiological information from an implanted diagnostic device, and then wirelessly interacts with an implanted therapeutic device to optimize therapy based on the physiological information, in alternative embodiments, the patient attachable device may wirelessly receive information from any implantable device, whether diagnostic or therapeutic, and interact with another implantable device, whether diagnostic or therapeutic. For example, the patient attachable device may wirelessly receive information from an implantable therapeutic device indicating that it has just completed or ceased performing a function, and based on the receipt of this information, interacts with a therapeutic device to perform another function or interacts with a diagnostic device to measure physiological information.

Although particular embodiments of the present invention have been shown and described, it should be understood that the above discussion is not intended to limit the present invention to these embodiments. It will be obvious to those skilled in the art that various changes and modifications may be made without departing from the spirit and scope of the present invention. Thus, the present invention is intended to cover alternatives, modifications, and equivalents that may fall within the spirit and scope of the present invention as defined by the claims.

What is claimed is:

1. A medical system, comprising
an implantable therapeutic device configured for providing therapy to a patient;
an implantable diagnostic device configured for acquiring physiological information from a patient;
a patient attachable device operable as an intermediary between the implantable diagnostic device and the implantable therapeutic device, the patient attachable device including an acoustic transducer for wirelessly receiving the physiological information from the implantable diagnostic device, a non-acoustic transducer for wirelessly transmitting one or more therapeutic optimization parameters to the implantable therapeutic device to optimize the therapy provided to the patient, and a sensor for sensing at least one physiologic parameter within the patient;

wherein the patient attachable device is configured for deriving the one or more therapeutic optimization parameters based at least in part from the physiological information received from the implantable diagnostic device and the at least one physiologic parameter sensed by the patient attachable device; and wherein the one or more therapeutic optimization parameters are configured to modify a pre-programmed protocol within the implantable therapeutic device used for providing the therapy.

2. The medical system of claim 1 wherein the implantable diagnostic device includes an absolute pressure sensor and the patient attachable device includes a barometric pressure sensor.

3. A medical system, comprising an implantable pulse generator configured for providing electrical stimulus therapy to a patient;

an implantable pressure sensor configured for sensing blood pressure measurements within the patient; and a patient attachable device operable as an intermediary between the implantable pressure sensor and the implantable pulse generator, the patient attachable device including an acoustic transducer for wirelessly receiving the blood pressure measurements from the implantable pressure sensor, a non-acoustic transducer for wirelessly transmitting therapeutic optimization information to the implantable pulse generator to optimize the electrical stimulus therapy provided to the patient, and an electrocardiogram sensor for sensing electrical activity within the patient;

wherein the patient attachable device is configured for deriving the one or more therapeutic optimization parameters based at least in part from the physiologic information received from the implantable pressure sensor and the electrical activity sensed by the electrocardiogram sensor.

4. The medical system of claim 3, wherein the patient attachable device is configured for wirelessly communicating with an external computing device.

5. The medical system of claim 3, wherein the patient attachable device further includes a barometric pressure sensor configured for sensing ambient pressure measurements, and wherein the one or more therapeutic optimization parameters are derived based in part on the ambient pressure measurements.

6. The medical system of claim 3, wherein the implantable pressure sensor includes an electrical circuit, an energy storage device, a switch coupled between the electrical circuit and the energy storage device, and an acoustic transducer coupled to the switch.

7. The medical system of claim 6, wherein the acoustic transducer of the implantable pressure sensor is configured to receive an acoustic activation signal from the patient attachable device to activate the switch between a first state, in which current is limited from flowing from the energy storage device to the electrical circuit, and a second state, in which current flows from the energy storage device to the electrical circuit.

8. A medical system, comprising an implantable therapeutic device configured for providing therapy to a patient;

an implantable diagnostic device including an electrical circuit configured for acquiring physiological information from a patient when activated, an energy storage device, a switch coupled between the electrical circuit and the energy storage device, and an acoustic transducer coupled to the switch; and a patient attachable device operable as an intermediary between the implantable diagnostic device and the implantable therapeutic device, the patient attachable device including an acoustic transducer for wirelessly receiving the physiological information from the implantable diagnostic device and a non-acoustic transducer for wirelessly transmitting one or more therapeutic optimization parameters to the implantable therapeutic device to optimize the therapy provided to the patient;

wherein the acoustic transducer of the implantable diagnostic device is configured to receive an acoustic activation signal from the patient attachable device to activate the switch between a first state, in which current is limited from flowing from the energy storage device to the electrical circuit, and a second state, in which current flows from the energy storage device to the electrical circuit.

9. The medical system of claim 8, wherein the patient attachable device is configured for wirelessly receiving the physiological information from the implantable diagnostic device, and for wirelessly transmitting therapeutic optimization information to the implantable therapeutic device to optimize the therapy provided to the patient.

10. The medical system of claim 8, wherein the patient attachable device is configured for deriving one or more therapeutic optimization parameters from the physiological information, and the therapeutic optimization information comprises the one or more therapeutic optimization parameters.

11. The medical system of claim 8, wherein the patient attachable device is configured for wirelessly receiving the physiological information from the implantable diagnostic device, and for wirelessly controlling the implantable therapeutic device to provide the therapy.

12. The medical system of claim 8, wherein the patient attachable device further includes at least one sensor, and wherein the patient attachable device is configured for deriving the one or more therapeutic optimization parameters based at least in part from the physiological information received from the implantable diagnostic device and one or more measurements sensed by the patient attachable device.

13. The medical system of claim 12, wherein the patient attachable device is configured for deriving the one or more therapeutic optimization parameters based at least in part from the physiological information received from the implantable diagnostic device and the one or more measurements sensed by the patient attachable device.

14. The medical system of claim 8, wherein the patient attachable device includes an electrocardiogram sensor for sensing electrical activity within the patient, and wherein the patient attachable device is configured for deriving the one or more therapeutic optimization parameters based at least in part on electrical activity sensed by the patient attachable device.

15. The medical system of claim 8, wherein the implantable diagnostic device includes an absolute pressure sensor and the patient attachable device includes a barometric pressure sensor.

16. The medical system of claim 8, wherein the implantable diagnostic device comprises a pressure sensor.

17. The medical system of claim 8, wherein the implantable diagnostic device comprises one or more of a an accelerometer and strain gauge.

18. The medical system of claim 8, wherein the implantable therapeutic device comprises one or more of an Implantable Pulse Generator (IPG) and a drug pump.

19. The medical system of claim 8, wherein the patient attachable device is configured for wirelessly communicating with an external computing device.

20. The medical system of claim 8, wherein the external computing device is configured to prompt the patient attachable device to transmit the acoustic activation signal.

* * * * *